US006334444B1

(12) United States Patent
Sisco

(10) Patent No.: US 6,334,444 B1
(45) Date of Patent: Jan. 1, 2002

(54) INMATE ESCORT RESTRAINT

(76) Inventor: Vernon G. Sisco, 1203 Catina Dr., Nashville, TN (US) 37217

( * ) Notice: Subject to any disclaimer, the term of this patent is extended or adjusted under 35 U.S.C. 154(b) by 0 days.

(21) Appl. No.: 09/637,732

(22) Filed: Aug. 11, 2000

(51) Int. Cl.[7] .............................................. A61B 19/00

(52) U.S. Cl. ...................... 128/869; 128/876; 128/878; 70/16

(58) Field of Search ............................... 128/869, 876, 128/878, 879; 70/14, 16, 18; 119/804, 816, 819

(56) References Cited

U.S. PATENT DOCUMENTS

| | | | | | |
|---|---|---|---|---|---|
| 567,049 | A | | 9/1896 | Smith | |
| 1,478,999 | A | | 1/1924 | Johnson | |
| 1,803,280 | A | | 4/1931 | Stull et al. | |
| 1,883,598 | A | | 10/1932 | Dahl | |
| 2,582,339 | A | | 1/1952 | Krueger | |
| 3,319,609 | A | | 5/1967 | Pickard et al. | |
| 4,854,138 | A | | 8/1989 | Charland | |
| 4,910,831 | A | * | 3/1990 | Bingold | 128/878 |
| 5,099,662 | A | | 3/1992 | Tsai | |
| 5,345,947 | A | * | 9/1994 | Fisher | 128/878 |
| 5,443,155 | A | | 8/1995 | Robinson | |
| 5,460,373 | A | | 10/1995 | McNutt | |
| D366,129 | S | | 1/1996 | Escone, III | |
| 5,518,010 | A | * | 5/1996 | Dodge | 128/869 |
| 5,680,781 | A | | 10/1997 | Bonds | |
| 5,732,576 | A | * | 3/1998 | Moore | 70/16 |
| 5,797,404 | A | | 8/1998 | Stanchin, II | |
| 6,012,416 | A | * | 1/2000 | Lammurs | 119/804 |

* cited by examiner

*Primary Examiner*—Michael A. Brown
(74) *Attorney, Agent, or Firm*—Waddey & Patterson; Emily A. Shouse

(57) ABSTRACT

A wrist restraint apparatus includes two straps threaded through an outer sleeve. By grasping the outer sleeve at a thumb-rest with one hand, a user can use his other hand to pull the outer sleeve to the rear, thus tightening the straps around the wrists of a restrained person. The length of the straps can then be secured by rotating the outer sleeve until the locking pin engages the appropriate notch in the locking channel port. To loosen or remove the straps, the outer sleeve is pulled slightly to the rear and rotated so that the locking pin disengages from the locking channel port. Once the device is applied, additional restraints, such as standard handcuffs or ankle cuffs, can be used if necessary to meet custody and control level escort requirements. The device acts as a handle to provide control over the inmate from the rear. The connection ring allows for the addition of a strap or chain to allow the individual to be restrained to a specific location or to allow a greater distance between the officer and the inmate during escort.

25 Claims, 5 Drawing Sheets

INMATE ESCORT RESTRAINT

BACKGROUND OF THE INVENTION

The present invention relates generally to a restraint device for use on humans. More particularly, this invention pertains to a wrist restraint device that humanely and securely restrains a person's hands behind their back while functioning as a handle to provide a means of controlling the person from the rear and as a means to limit the movement of the restrained individual to a certain area.

The device was designed to be a humane restraint with ease of use to fill a long-standing need for more safety and control in the process of restraining, removing, and escorting violent inmates from their cells to and from facility activities.

Various types and constructions of flexible material wrist restraints for use by law enforcement personnel in dealing with subduing suspects and controlling prisoners are known. Such restraints in most instances are made of a polymeric based material and embody strap parts which can be formed into loops for girding both wrists of a person, and means to secure or lock the loops, the locking means commonly being teeth or projections carried on the strap parts and a cooperating latch or stop usually carried elsewhere on the strap parts for engaging the teeth or projections to effect a stop function which maintains the loops secured.

Representative of the mentioned constructions are U.S. Pat. Nos. 4,071,023; 4,909,051; 4,910,831; 5,088,158 and 5,159,728. These patents disclose generally flat strap parts for use as the loop forming component.

U.S. Pat. Nos. 1,803,280; 5,443,155; and 5,680,781 disclose restraint devices which are modified handcuffs with handles. However, they do not disclose a means to attach the restraint to a cell door or to the user, allowing for more control and greater distance from the restrained individual.

U.S. Pat. Nos. 567,049; 1,478,999; 1,883,598; 2,582,339; and 3,319,609 teach restraint devices for holding animals, in particular pigs. Although these devices each have a loop which can be tightened, they are designed to hold the snout, or some other body part, of an animal and are not suitable for use on humans.

Other restraint devices are disclosed in U.S. Pat. Nos. 4,854,138; 5,460,373; 5,797,404; and 5,099,662. However, none of these devices provide the level of control and ability to restrict the restrained person's area of movement offered by the present invention.

What is needed, then, is a restraint device that effectively and humanely restrains the hands of a person while providing superior control and safety to the officer, including providing a means for releasably attaching the restraint and thus the restrained person, to a cell door or to the officer.

SUMMARY OF THE INVENTION

Before an inmate's cell door is opened, the inmate's hands would be restrained behind his back through a mid-level cell door pass-through, with the device attached to the cell door. When using the device in this manner, the inmate's area of movement is restricted. Once the device is applied, the cell door can be opened and additional restraints, such as standard handcuffs or ankle cuffs, can be used if necessary to meet custody and control level escort requirements. The inmate would remain restrained at and to the cell door until the officer has the level of control required for a safe escort. The device acts as a handle to provide control over the inmate from the rear. The connection ring allows for the addition of a strap (nylon, leather) or chain to allow the individual to be restrained to a specific location or to allow a greater distance between the officer and the inmate during escort.

To operate the device, an individual's hands are placed behind his back and inserted into the straps. Holding the device at the thumb-rest with one hand, the user uses his other hand to pull the outer sleeve to the rear (away from the individual being restrained) until the straps reach the desired tightness and then rotates the outer sleeve to the right (clockwise) until the locking pin engages the appropriate notch in the locking channel port. To loosen the straps, the outer sleeve is pulled slightly to the rear and rotated to the left so that the locking pin disengages from the locking channel port.

Accordingly, it is an object of this invention to provide an effective means for restraining a person.

It is a further object of this invention to provide a restraint which can be applied through the pass-through of a cell door.

It is a further object of this invention to provide a restraint which restricts movement of a person to a limited area so that additional restraints may be applied.

DESCRIPTION OF THE PREFERRED EMBODIMENTS

Figure 1:
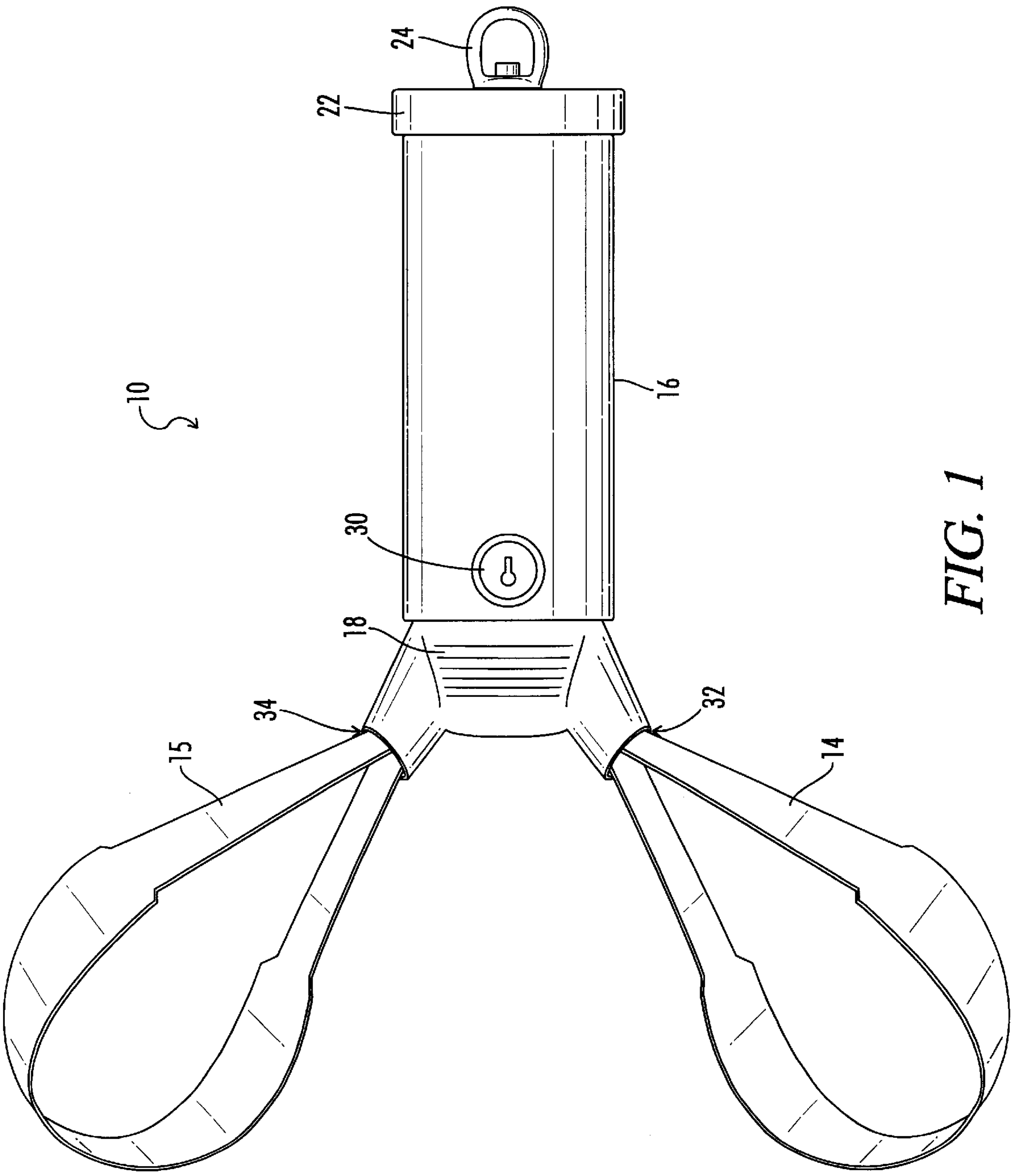
FIG. 1 is a top view of the present invention.
Figure 2:
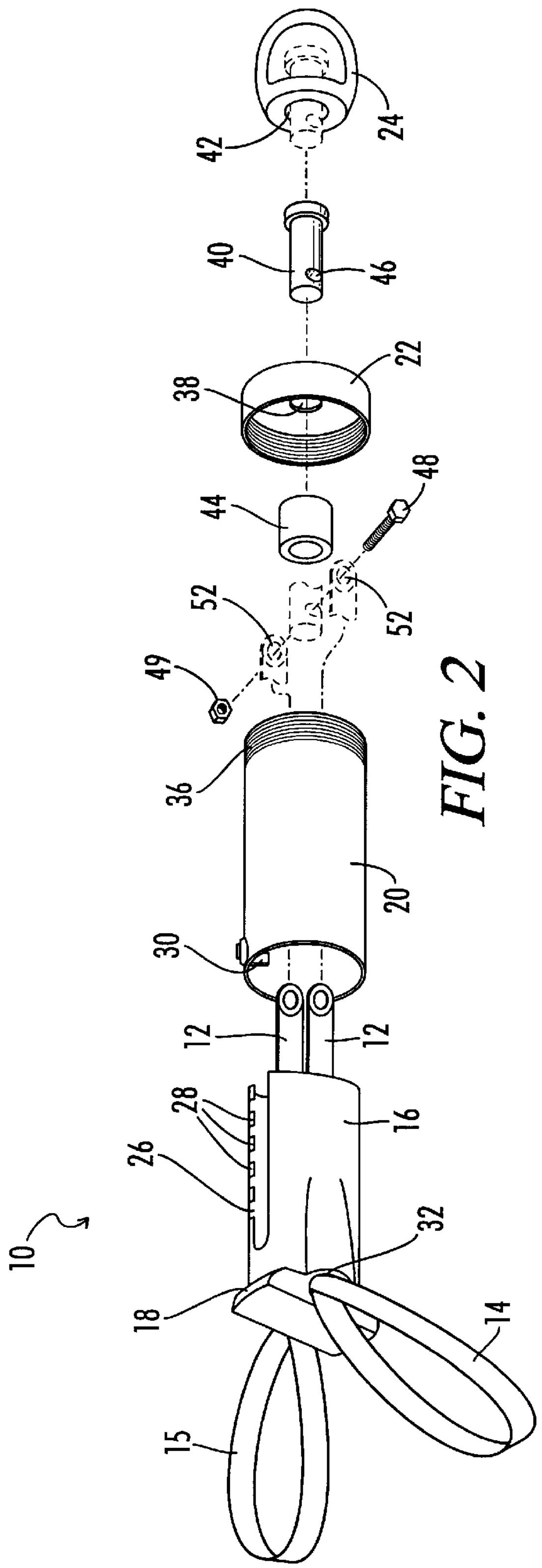
FIG. 2 is an exploded view of the present invention.

Referring now to the drawings, wherein like reference numerals refer to like parts throughout, the restraint device of the present invention is referred to generally as 10. As shown in FIGS. 1 and 2, the restraint device comprises a strap 12 which forms two loops 14, 15. It is also contemplated that two straps could be utilized such that each strap formed one loop of the invention. The loops 14, 15 are threaded through a housing 16, or cylindrical housing 16. At the end of the housing 16 proximate the loops 14, 15, a thumb rest 18 is formed in the housing 16 to provide for a more secure grip on the device 10. Integrally formed in the housing 16 is a locking channel 26 having multiple notches 28.

Sleeve 20, or housing sleeve 20, is a hollow cylinder which is slideable over the outside surface of the housing 16. Locking pin 30 in the sleeve 20 is configured to engage the notches 28 in the locking channel 26. In a preferred embodiment, locking pin 30 is integrally formed in sleeve 20. However, it is contemplated that the locking pin 30 may be attached by any means known to one of skill in the art.

The strap 12 is looped inside the housing 16 such that it exits the housing 16 at hole 32, forms loop 14, re-enters the housing at hole 32, then exits the housing at to hole 34, forms loops 15, and re-enters the housing at hole 34. In the preferred embodiment, holes 32 and 34 are located on opposite sides of thumb rest 18. The ends of strap 12 then run through housing 16, away from loops 14, 15 and attach to the sleeve 20.

Restraint connection ring 24 is attached to the sleeve 20 to provide a means for attaching the restraint device 10 to a door or other suitable object or to a person escorting the restrained individual.

Figure 3A:
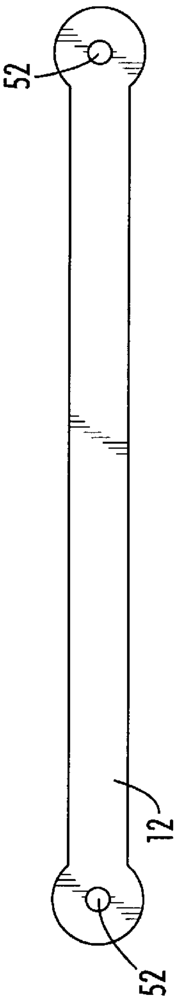
FIG. 3 is a view of two alternate straps for the present invention.
Figure 3B:
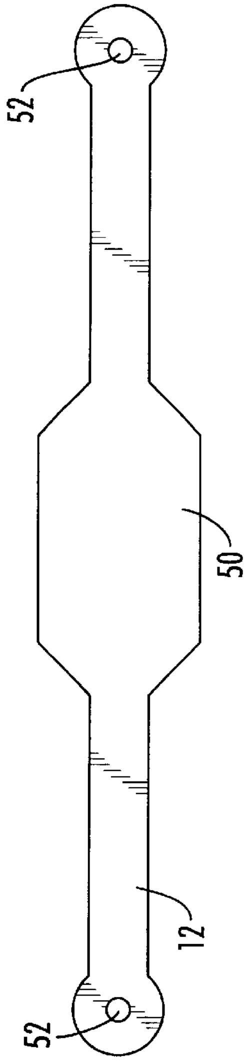

FIGS. 3A and 3B show two embodiments of strap 12. In a preferred embodiment, strap 12 is a semi-rigid flat material formed from nylon or nylon 66, although it is contemplated that strap 12 could be formed from any number of materials known to one of skill in the art. Further, in a preferred embodiment shown in FIG. 3B, the middle portion 50 of strap 12 has a greater diameter than the end portions of strap 12. FIG. 1 also shows this embodiment of strap 12. Strap 12 having a wider middle portion 50 provides for greater control over the hands of the restrained individual and reduces, if not eliminates, the possibility of restraint manipulation. FIG. 3A shows an embodiment of strap 12 in which the middle portion has a diameter which is less than the diameter of the end portion. It is also contemplated that the diameter of the middle portion could be equal to the diameter of the end portions. Strap 12 also has holes 52, or first and second openings 52, in each end which are used to attach strap 12 to sleeve 20.

In a preferred embodiment, one end 36 of sleeve 20 is threaded to receive end cap 22, which is also threaded. End cap 22 has a hole 38 in its center.

In a preferred embodiment, restraint connection ring 24 is attached to sleeve by means of end cap 22. Pin 40, having a head with a greater diameter than the diameter of hole 38 of end cap 22, is inserted through an opening 42 in restraint connection ring 24, then inserted through hole 38 in end cap 22 and secured to attach restraint connection ring 24 to end cap 22. End cap 22 is then screwed onto sleeve 20.

In a preferred embodiment, pin 40 is the means by which strap 12 is attached to sleeve 20. After pin 40 is inserted into hole 38 of end cap 22, it is inserted through spacer 44. Holes 52 in the ends of strap 12 are then aligned with the hole 46 in pin 40. Screw 48 is inserted through holes 52 and 46 and then secured in nut 49, to securely attach both ends of strap 12 to end cap 22, which is then screwed onto sleeve 20.

Figure 4:
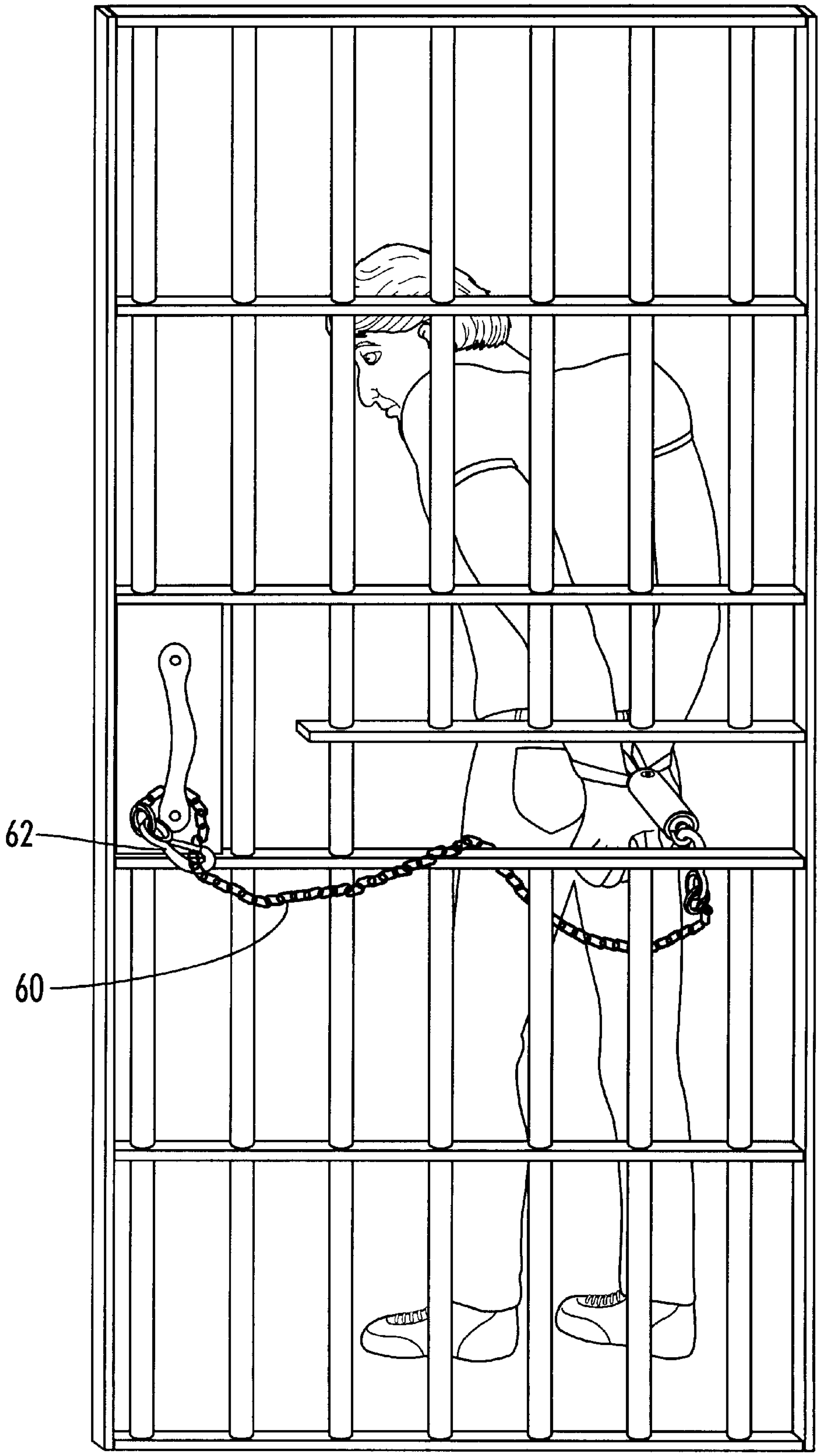
FIG. 4 is a view of the present invention used to restrain a inmate to a cell door.
Figure 5:
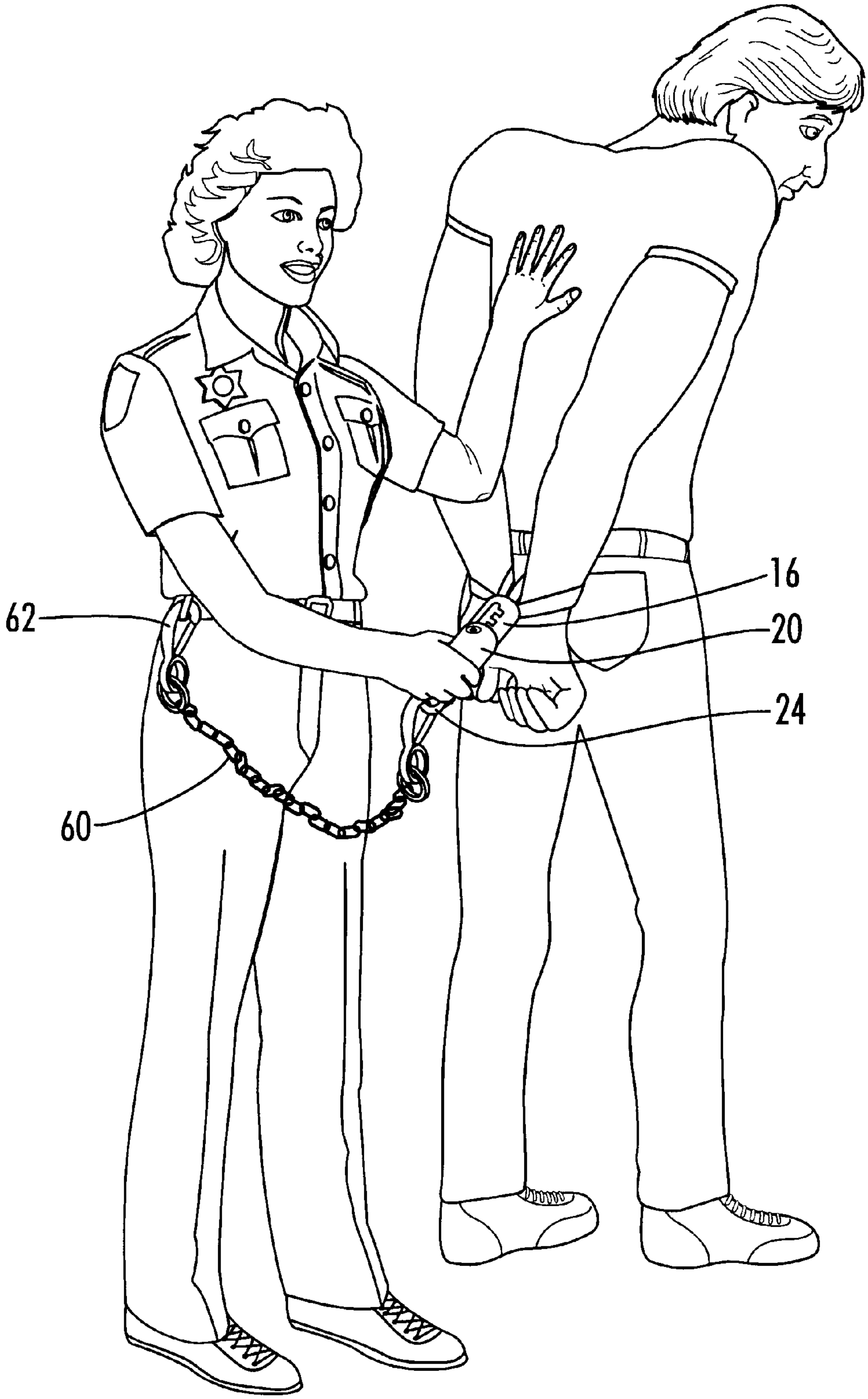
FIG. 5 is a view of the present invention used to escort an inmate.
Figure 6:
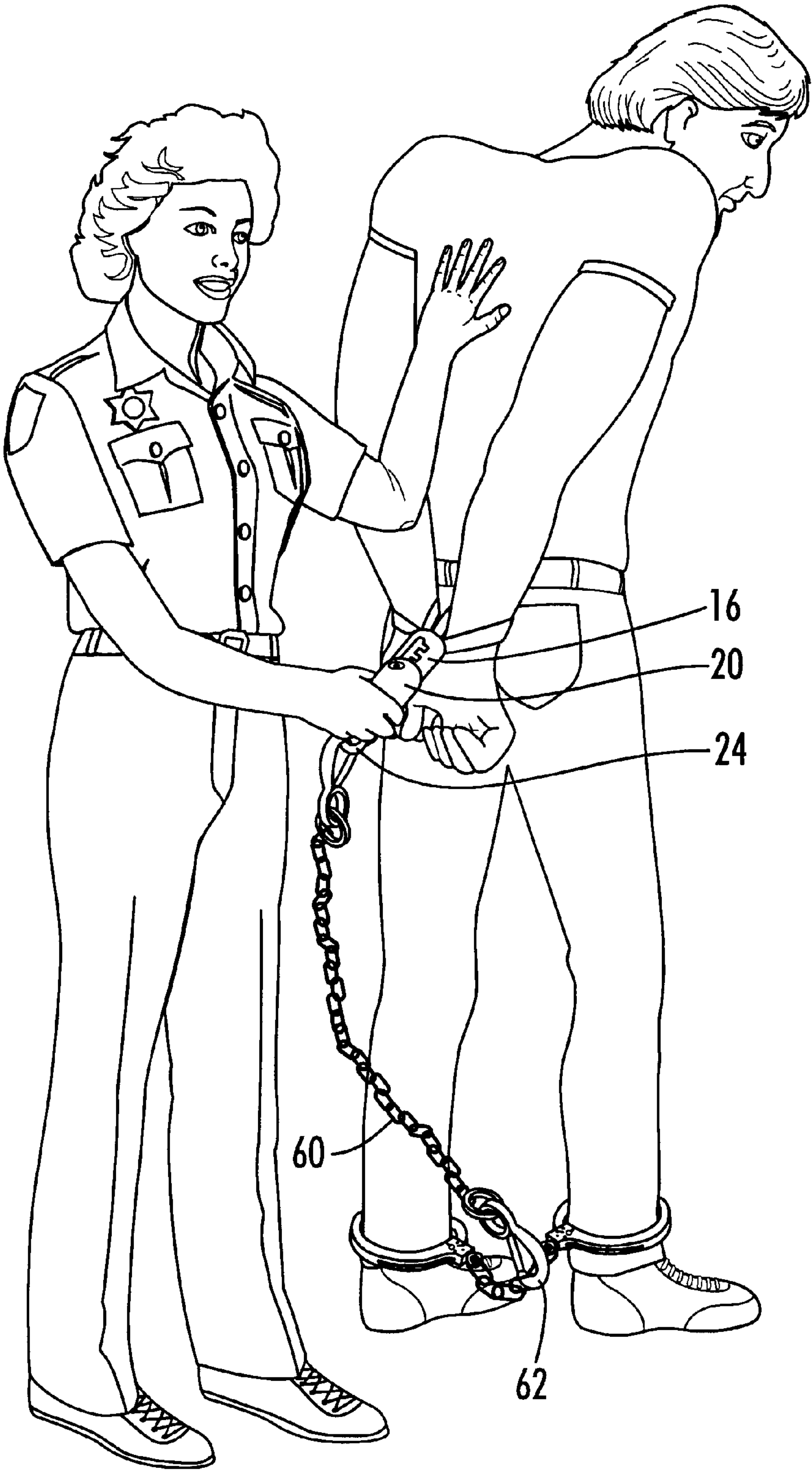
FIG. 6 is a view of the present invention used with leg cuffs.

In one embodiment illustrated in FIGS. 4 and 5, restraint device 10 also includes a fetter 60, or leash 60 or restraint strap 60, which is attached to restraint device 10, preferably at restraint connection ring 24. Fetter 60 can be used to restrain an individual's movement by attaching the end of fetter 60 not attached to restrain device 10 to an object, such as a cell door, or another person, such as an officer escorting the restrained individual. As shown in FIG. 6, fetter 60 may also be attached to leg cuffs on the restrained individual. This restraint technique will further restrict the restrained individual's gait of walk simply by lifting up on device 10. The attachment is accomplished by catch 62. It is contemplated that numerous different types of catches could operate effectively. Fetter 60 may be a length of metal chain, nylon leather or any other material known to one of skill in the art.

FIG. 4 illustrates how a restrained individual's movement can be further limited by attaching fetter 60 to a cell door. FIG. 5 illustrates how a restrained individual can be further controlled during escort by attaching fetter 60 to the escorting officer.

Method of Restraining a Person's Hands

The hands of the person to be restrained are inserted into the loops 14, 15 of the restraint device 10, one hand in each loop, until the loops 14, 15 are around the person's wrists. The officer grasps the device 10 in one hand, with the thumb of that hand on the thumb rest 18 and tightens the loops 14, 15 by using the other hand to pull the housing sleeve 20 in a rearward direction away from the restrained person until the loops 14, 15 reach the desired level of tightness. The housing sleeve 20 is then rotated until it engages a notch 28 in the housing 16 to secure the loops 14, 15 about the wrists. A restraint strap 60 is attached to the housing 16 and to another object such as a cell door or an officer.

To remove the restraint device 10, housing sleeve 20 is pulled in a rearward direction and rotated in the opposite direction until it disengages from notch 28 in housing 16 to loosen loops 14, 15 for removal from a person's wrists. The restraint device 10 may be applied and removed through the pass-through of a cell door.

Thus, although there have been described particular embodiments of the present invention of a new and useful "Inmate Escort Restraint", it is not intended that such references be construed as limitations upon the scope of this invention except as set forth in the following claims.

What is claimed is:

1. A restraint device comprising:

two loops formed from a strap;

a housing through which the ends of said strap are inserted;

a locking channel having multiple notches integrally formed in said housing;

a thumb rest formed on said housing;

a sleeve, slideable over the outside surface of said housing;

a locking pin integrally formed in said sleeve to engage said locking channel;

means for attaching said strap to said sleeve; and a restraint connection ring attached to said sleeve to removably attach the device to another object.

2. The device of claim 1 wherein said strap has two end portions joined by a center portion, said center portion forming said loop to restrain a wrist.

3. The device of claim 2 wherein said center portion of said strap is wider than said end portions.

4. The device of claim 2 wherein said center portion of said strap has a diameter equal to or less than the diameter of said end portions of said strap.

5. The device of claim 1 further comprising:

a fetter, having one end removably attached to said restraint connection ring; and a catch, attached to the end of said fetter opposite the end attached to said restraint connection ring (and removably attachable to other objects.

6. The device of claim 5 wherein said fetter is a metal chain.

7. The device of claim 5 wherein said fetter is nylon.

8. The device of claim 1 wherein said restraint connection ring is removably attachable to said sleeve.

9. The device of claim 1 further comprising holes in each end of said strap.

10. The device of claim 9 wherein said means for attaching said strap to said sleeve comprises:

a screw and a nut;

a spacer;

an end cap, threaded to engage said sleeve and having a hole through its center;

a pin, having a head with a diameter greater than the diameter of the hole in said end cap, and a stem having a hole through its end;

wherein said pin is inserted through said end cap hole and through said spacer such that the hole in said pin aligns with the holes in said strap for insertion of said screw which engages said nut to secure said strap to said sleeve when said end cap is screwed onto said sleeve.

11. A restraint device comprising:

a cylindrical housing;

two loops extending from said housing, said loops formed from a length of strap material;

a locking channel integrally formed in said housing;

a sleeve, slideable over the outside surface of said housing;

a locking pin integrally formed in said sleeve to engage said locking channel;

means for securing said loops to said sleeve; and a leash to removably attach the device to another object.

12. The device of claim 11 further comprising:

a thumb rest integrally formed on said housing.

13. The device of claim 11 further comprising:

a plurality of notches integrally formed along said locking channel.

14. The device of claim 11 further comprising:

an end cap releasably connected to said sleeve.

15. The device of claim 14 wherein said end cap includes a hole through its center.

16. The device of claim 14 wherein said leash is removably attached to said end cap.

17. The device of claim 14 wherein said means for attaching said loops to said sleeve comprises:

a spacer;

a pin, having a head with a diameter greater than the diameter of the hole in said end cap, and a stem having a hole through the end distal the head, wherein said pin is inserted through the hole in said end cap and through said spacer;

a first opening in the first end of said strap material;

a second opening in the second end of said strap material; and a screw and a nut wherein the openings in said strap material are aligned with the hole in said pin and said screw is inserted therethrough and into said nut.

18. The device of claim 11 wherein said leash is removably attached to said sleeve.

19. The device of claim 11 wherein said leash is a chain.

20. The device of claim 11 wherein said leash is nylon.

21. A method of restraining a person's hands comprising the steps of:

(a) inserting a person's hands into two loops protruding from a housing until the loops are around his wrists;

(b) grasping the housing;

(c) tightening the loops by pulling the housing sleeve to which the loops are attached in a rearward direction away from a person until the loops reach the desired level of tightness; and (d) rotating the housing sleeve until it engages a notch in the housing to secure the loops around the wrists.

22. The method of claim 21 further including the step of:

attaching a restraint strap to the housing sleeve and to a cell door to restrict a restrained person's area of movement.

23. The method of claim 21 further including the step of:

attaching a restraint strap to the housing sleeve and to a person escorting a restrained person.

24. The method of claim 21 further including the steps of:

pulling the housing sleeve in a rearward direction; and rotating the housing sleeve in the opposite direction until it disengages from the notch in the housing to remove the loops from a restrained person's wrists.

25. The method of claim 21 further including the step of:

attaching a restraint strap to the housing sleeve and to leg cuffs on a restrained person.

* * * * *